United States Patent [19]
Wagner

[11] Patent Number: 5,922,016
[45] Date of Patent: *Jul. 13, 1999

[54] APPARATUS FOR ELECTRIC STIMULATION OF AUDITORY NERVES OF A HUMAN BEING

[75] Inventor: Hermann Wagner, Berlin, Germany

[73] Assignees: Ingeborg Hochmair; Erwin Hochmair, both of Axams/Tirol, Austria

[*] Notice: This patent issued on a continued prosecution application filed under 37 CFR 1.53(d), and is subject to the twenty year patent term provisions of 35 U.S.C. 154(a)(2).

[21] Appl. No.: 08/590,567

[22] Filed: Jan. 26, 1996

[51] Int. Cl.$^6$ ........................................................ A61F 2/18
[52] U.S. Cl. .......................... 607/137; 600/559; 128/898
[58] Field of Search ................................. 607/55, 56, 136, 607/137; 128/898; 381/312, 60; 600/559

[56] References Cited

U.S. PATENT DOCUMENTS

| | | | |
|---|---|---|---|
| 3,799,146 | 3/1974 | John et al. | 128/2.1 |
| 4,535,785 | 8/1985 | Van Den Honert et al. | 128/746 |
| 4,577,641 | 3/1986 | Hochmair et al. | 128/746 |
| 4,858,612 | 8/1989 | Stocklin | 607/136 |
| 5,119,826 | 6/1992 | Baart De La Faille | 128/746 |
| 5,291,785 | 3/1994 | Downs | 73/585 |
| 5,395,301 | 3/1995 | Russek | 601/41 |

*Primary Examiner*—Jack W. Lavinder
*Assistant Examiner*—David M Ruddy
*Attorney, Agent, or Firm*—Henry M. Feiereisen

[57] ABSTRACT

Apparatus for electric stimulation and diagnostics of auditory nerves of a human being, e.g. for determination of sensation level (SL), most conformable level (MCL) and uncomfortable level (UCL) audibility curves, includes a stimulator detachably secured to a human being for sending a signal into a human ear, and an electrode placed within the human ear and electrically connected to the stimulator by an electric conductor for conducting the signals from the stimulator into the ear. A control unit is operatively connected to the stimulator for instructing the stimulator as to characteristics of the generated signals being transmitted to the ear.

9 Claims, 8 Drawing Sheets

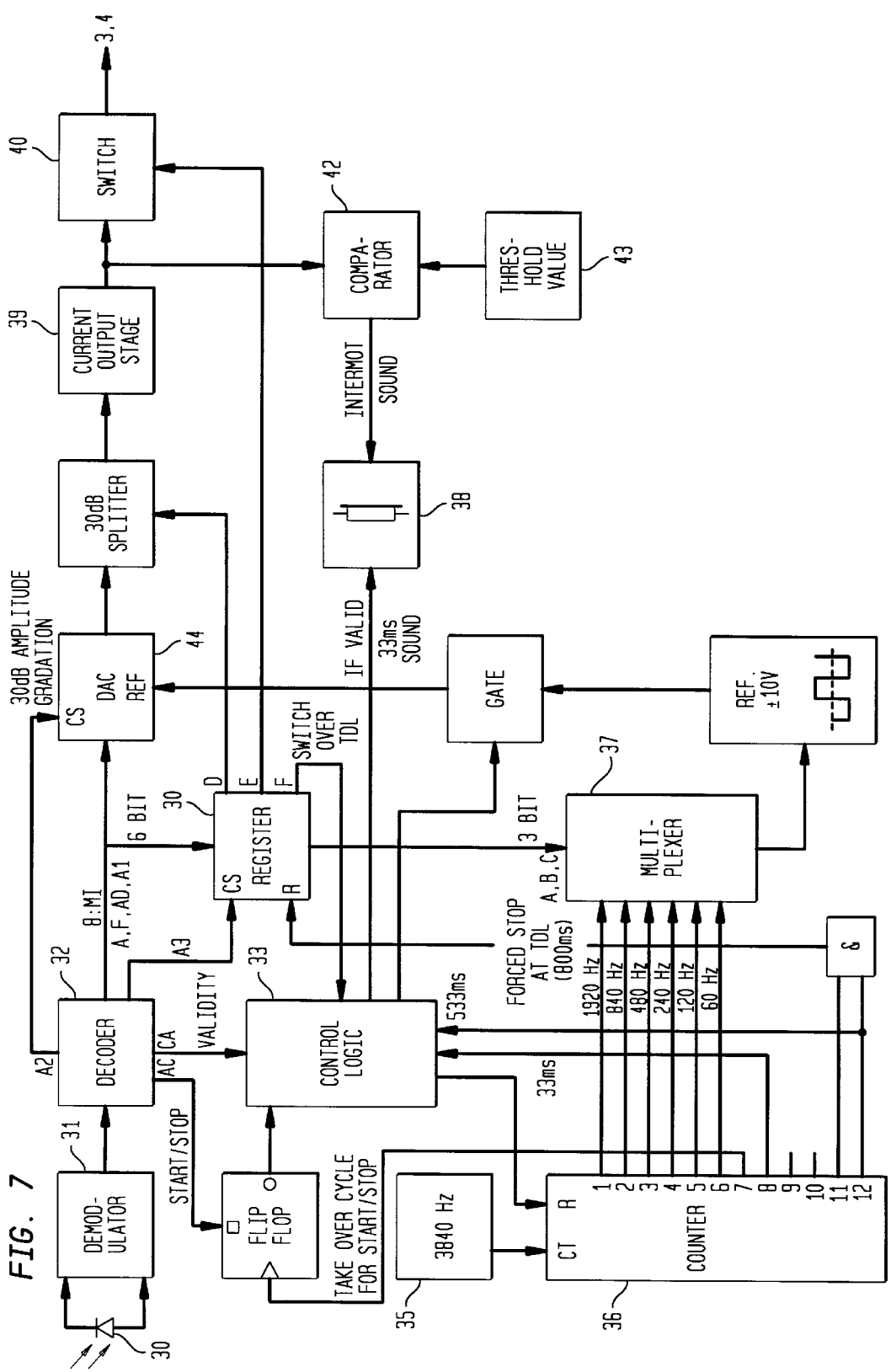

APPARATUS FOR ELECTRIC STIMULATION OF AUDITORY NERVES OF A HUMAN BEING

BACKGROUND OF THE INVENTION

The present invention refers to an apparatus for electric stimulation and diagnostics of the auditory nerves of a human being, in particular for determination of sensation level, most comfortable level and uncomfortable level curves of the auditory meatus.

In most deaf people, the transmission of electrical impulses from the internal ear to the brain is fully functional. The reason for deafness resides primarily in malfunctions of the so-called hair cell which is located within the internal ear and responsible for converting mechanical sound oscillations into electrical neural impulses. In cases of such defects, the auditory nerves can be stimulated directly by electrical impulses which are generated preferably by an implanted electronic circuitry via electrodes implanted in or near the cochlea. The surgical procedure for inserting the implant into the head is however not only stressful to the patient but also complex and thus expensive. As deafness may however also be the result of a defective transmission of electrical impulses, it is indeed conceivable that without evaluation of the functionality of the concerned auditory nerves, the implantation may turn out to be of no value.

SUMMARY OF THE INVENTION

It is an object of the present invention to provide an improved apparatus for electrical stimulation and diagnostics of auditory nerves, which allows determination in advance, even in very sensitive and uncooperative patients such as infants, whether the transmission of stimuli of the auditory nerves is functional or at least sufficiently functional to justify an artificial stimulation through implantation of cochlea electrodes.

This object, and others which will become apparent hereinafter, are attained in accordance with the present invention by providing a stimulator which is adapted for detachable securement to the clothing of a human for generating signals, electrodes placed within the human ear and electrically connected to the stimulator by an electric conductor for conducting the signals from the stimulator into the human ear, and a control unit operatively connected to the stimulator for instructing the stimulator as to characteristics of the generated signals being transmitted.

As the stimulator for generating the required impulses is easy to handle, the person being examined is inconvenienced only in a very minor way. Suitably, the electrodes may be placed within the auditory meatus or in the middle ear.

The electrodes that are placed within the auditory meatus are formed by a body of electrically conducting material such as e.g. graphite, metal or the like and connected via an electric conductor to the stimulator, whereby the conductor is secured in place by an enveloping plastic body of elastically deformable material which bears upon the inside wall of the auditory meatus and may also be used for sealing the auditory meatus. Thus, the stimulation impulses can be transmitted in a particular effective manner to the auditory nerves while the elastic plastic body securely retains the electrode in place within the auditory meatus.

When being placed in the middle ear, preferably upon the promontory, the electrode are provided in form of a body of electrically conducting material such as graphite, metal or the like, which is situated at the end of an insulated metal rod with electrical conduction. The metal rod is formed preferably in crank-like manner and is secured in place by an enveloping plastic body of elastically deformable material that bears upon the inner wall of the auditory meatus. If necessary, the metal rod may further be secured by an adhesive strip upon the wall surface of the auditory meatus. A placement of the electrode in this manner is particularly effective to stimulate the auditory nerves.

Preferably, the control unit is of a type to enable a selection of the time pattern as well as intensity and frequency of the stimulation signals for wireless transmission, e.g. infrared transmission, to the stimulator. Thus, the stimulator becomes easy to manipulate while the person being examined retains full freedom of movement. The transmitter as well as receiver for wireless transmission can be produced in a simple manner while still affording the required range for use with young children.

According to another feature of the present invention, the stimulator is equipped with means for triggering an acoustic confirmation signal when receiving data from the control unit to effect the intended stimulation. The generation of the acoustic signal confirms the correctness of the data transmission in a simple manner. Preferably, the stimulator may further include means for triggering acoustic warning signals in case of malfunction of the intended stimulation or reception of incorrect data. Thus, the determination of characteristic audibility curves will not be adversely effected. Suitably, the triggered warning signal is differentiated in dependence on the cause for malfunction. This enables the user to pinpoint the error source as to whether it is based on apparative malfunction, or possible screening of the receiver diode of the stimulator, or misplaced electrodes, or even on discharged batteries.

In accordance with another feature of the present invention, the stimulator is provided with a separate optical signaling device which triggers an optical signal during transmission of a stimulation signal in one of both auditory meatus or in one of both middle ears. Thus, psychological conditioning methods as known from pediatric audiometry are employed for reinforcing the reaction during perception of a stimulus, with the an additional optical control of the stimulation being accomplished in a simpler manner. The optical signaling device may be a simple toy, such as a toy truck, which is suitable for infants. During examination, the transmission of a stimulation signal triggers at the same time an optical signal that draws the attention of the infant. This reaction provides the operator with a clear and unmistakable sign that the infant senses an auditive signal.

Suitably, the control unit includes a graphic display for illustration of determined audibility curves and associated numerical values. Thus, characteristic audibility curves can be monitored during examination, and obviously erroneous values can be corrected by renewed measurements. Advantageously, the control unit has a terminal for attachment of a printer to thereby provide the operator with a printout of the characteristic audibility curves as determined for the auditory meatus of a patient.

BRIEF DESCRIPTION OF THE DRAWING

The above and other objects, features and advantages of the present invention will now be described in more detail with reference to the accompanying drawing in which:

FIG. 6b is a schematic illustration of the back panel of the control unit of FIG. 6a; and FIG. 7 is a schematic illustration of a circuitry in form of a block diagram, showing various components of the stimulator according to the present invention.

DETAILED DESCRIPTION OF PREFERRED EMBODIMENTS

The sensory perception "hearing" is created in a normally hearing human being by the vibrations of the ear drum through sound waves that enter the ear. These vibrations are converted in the internal ear into electrical neural impulses which are sent to the brain via the auditory nerves for actual recognition. In cases in which the conversion of the mechanical oscillations of the ear drum into electrical neural impulses is defective, no acoustic perception takes place. In deaf human beings which have such a dysfunctional internal ear, the conversion of the sound waves can however be assumed by an electronic circuitry by which the auditory nerves is excited directly with electrical impulses via an electrode implanted in the cochlea so that the hearing capability can at least be partially restored. In order to achieve the desired results through the cochlea implant, the auditory nerves must at least be partially functional in order to effect a transmission of electrical impulses to the brain.

Such cochlea implants are especially suitable for deaf infants because a successful implant of a cochlea electrode with pertaining sound converter before the infant reaches the age of speech acquisition can prevent muteness which is a consequence of deafness so that the child can acquire speech in the infant stage like healthy children. The success of such cochlea implants depends upon the functionality and ableness of the auditory nerve so that a determination of the effectiveness of the auditory nerve before implantation becomes desirable.

A reliable information about the functional capability of the auditory nerves requires a determination of the sound pressure commensurate with the so-called sensation level (SL) which is the pressure level of a sound expressed in decibels above its threshold of audibility for the individual, and of the uncomfortable level (UCL) of each ear. The determination of the characteristic audibility curve of the sensation level is effected by stimulating the auditory nerve at a certain frequency. The intensity of the stimulation, i.e. pressure level, is then gradually increased until the patient positively identifies an auditive perception. This process is repeated in a same manner at different frequencies. The connection of the family of points determined in this manner represents the SL characteristic audibility curve.

The UCL characteristic audibility curve is determined in a same manner whereby the sound intensity in decibels for stimulating the auditory nerves is increased at each frequency to such a degree that the patient experiences an uncomfortable auditive perception. The connection of the family of points as determined in this manner represents the UCL characteristic audibility curve.

Figure 1:
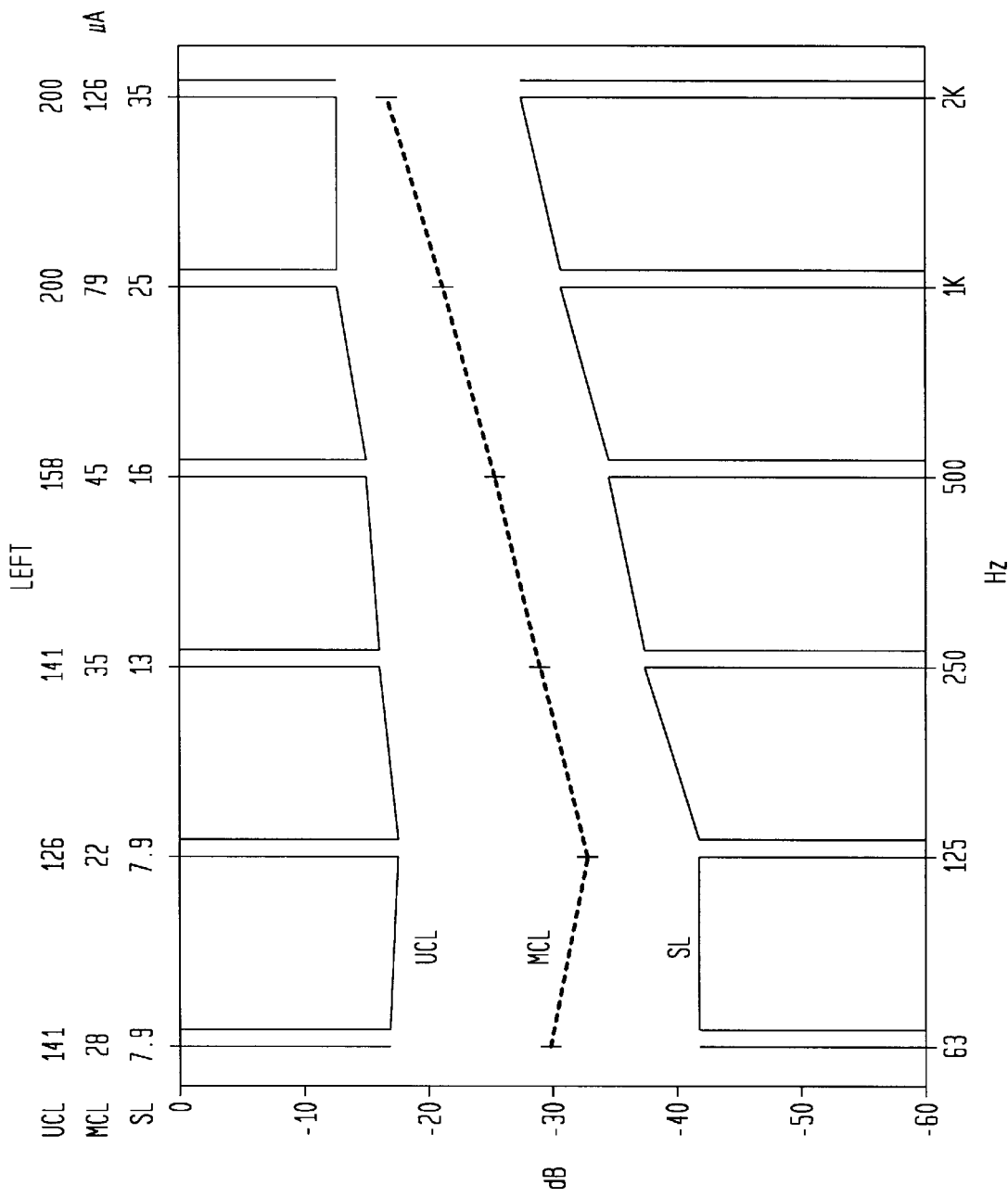
FIG. 1 shows a graphical illustration as well as numerical value illustratior of the pressure level of an audiogram of an auditory nerve suitable for implantation, commensurate with the sensation level (SL), most comfortable level (MCL) and uncomfortable level (UCL), expressed in decibels as a function of the frequency in hertz (Hz), as determined by an apparatus for electric stimulation of the auditory nerves in accordance with the present invention.

In FIG. 1, the SL characteristic audibility curve and UCL audibility curve are plotted by measuring range of sound intensities in decibels (db) against the sound frequencies in hertz (Hz) in a frequency range of the stimulation signals between 63 to 2,000 Hz for an able auditory nerve. The area between the SL audibility curve and the UCL audibility curve represents the MCL characteristic audibility curve (most comfortable level) which displays those sound intensities at different frequencies that are perceived by the patient as comfortable sound level. The determination of the most comfortable level is however relative difficult to ascertain in infants and is of secondary relevance for evaluating the suitability of a cochlea implant.

Figure 2A:
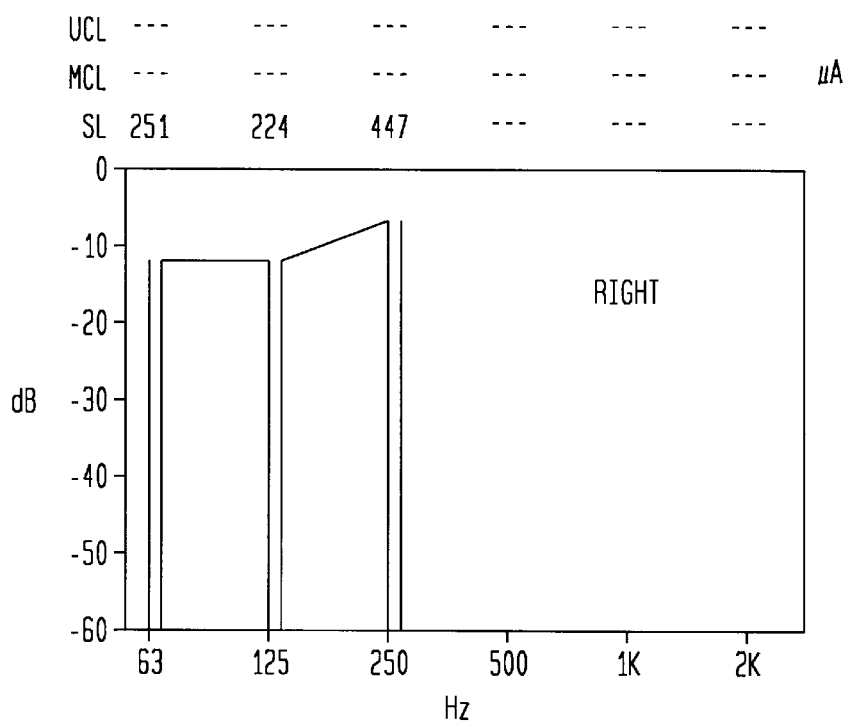
FIG. 2a is a graphical illustration of the sensation level and uncomfortable level of the right auditory nerve of a deaf infant, indicating that the examined auditory nerve is most likely unsuitable for implantation.
Figure 2B:
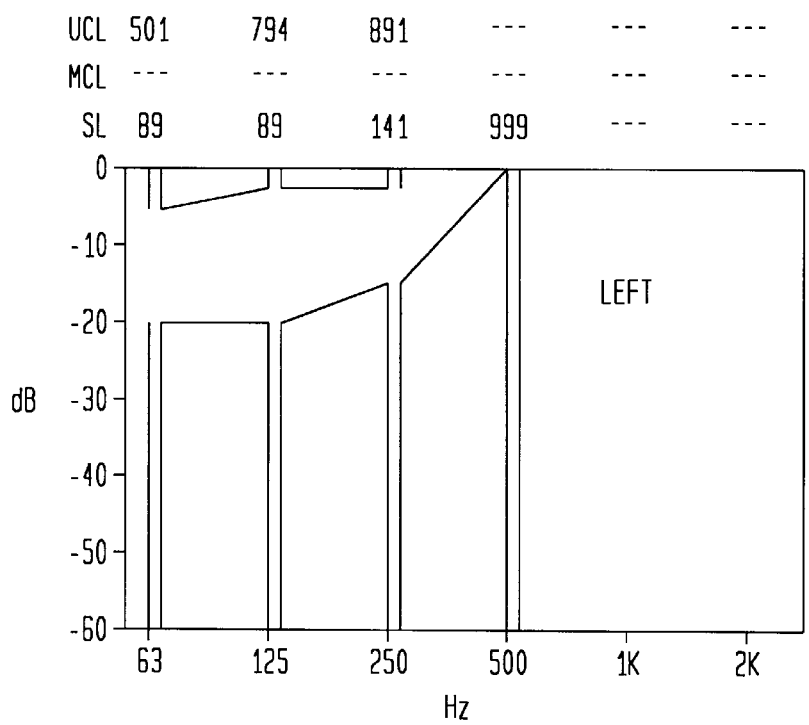
FIG. 2b is a graphical illustration of the sensation level and uncomfortable level of the left auditory nerve of a deaf infant, indicating that the examined auditory nerve is most likely unsuitable for implantation.

FIGS. 2a and 2b depict the SL audibility curve and UCL audibility curve of the right and left auditory nerves of a deaf infant, and it can be seen that the suitability of the auditory nerves for a cochlea implant is at best doubtful. An auditive perception is created in the right auditory meatus only at a very intense stimulation at low frequencies while frequencies exceeding 250 Hz cannot be perceived at all. The left auditory meatus also perceives sounds only at very low stimulation frequencies. Based on the pattern of these audibility curves, the specialist can ascertain the appropriateness of a cochlea implant and the surgical procedure.

The determination of these audibility curves for deaf infants has proven very difficult up to now because of the inability to precisely ascertain if and when an auditive perception has actually occurred. It should be noted in this context that persons skilled in the art will understand that the stimulation apparatus according to the present invention should not be limited to applications with infants but is applicable for diagnostic purposes for persons of any age group. However, since the determination of audibility curves poses a particular problem when applied for infants, the following description refers primarily to the use of the stimulation apparatus for infants.

Figure 3:
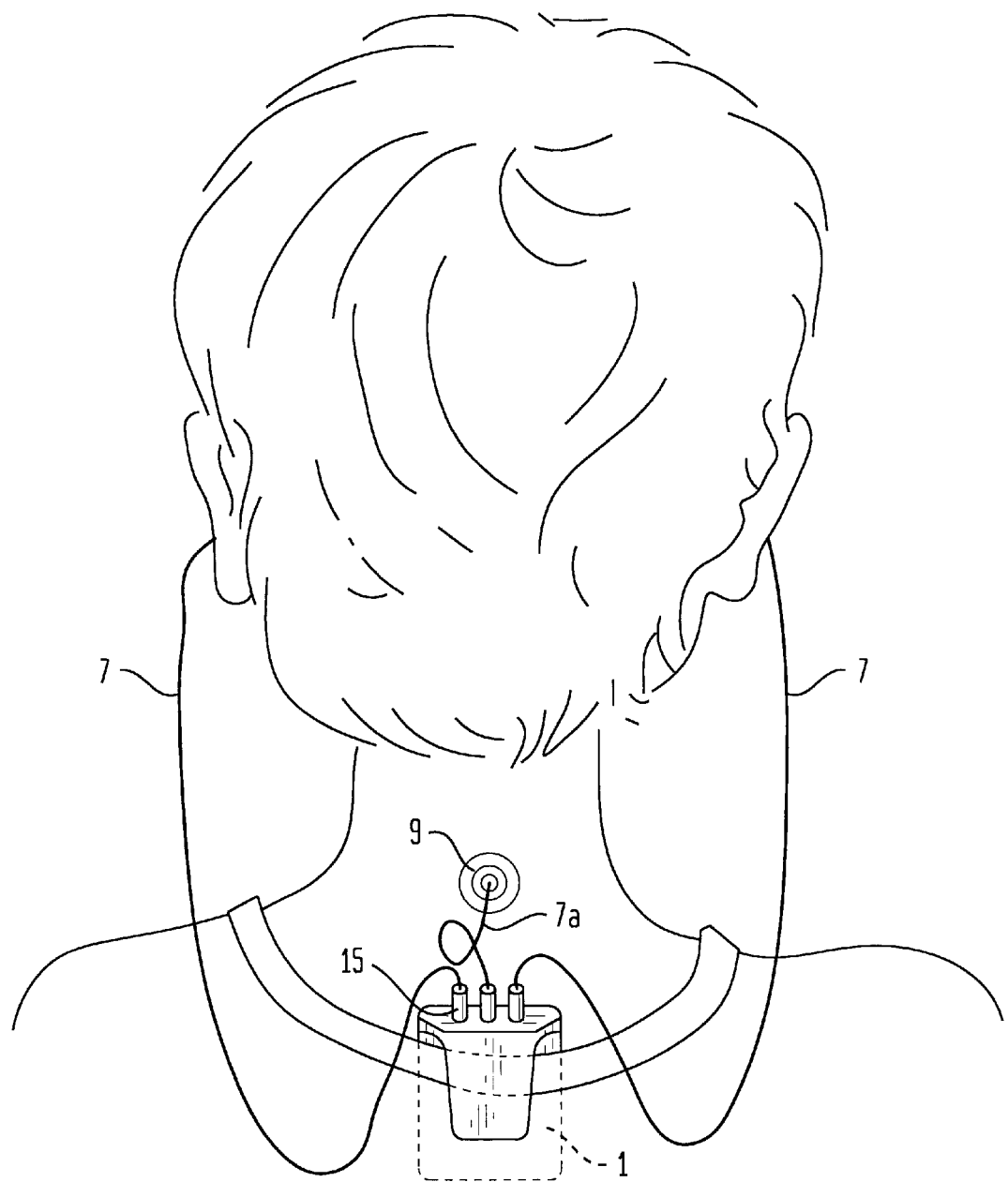
FIG. 3 is a schematic illustration of a stimulator according to the present invention as attached to the body of a patient.

Turning now to FIG. 3, there is shown one embodiment of a stimulating apparatus according to the present invention, including a stimulator 1 which is secured to the clothing of a child being examined and formed with various terminals 15 for connection of conductors. Two conductors 7 are respectively routed to the ears of the patient, and one conductor 7a is connected to a mass electrode 9 that is attached on the skin of the patient, e.g. of the neck.

Figure 4A:
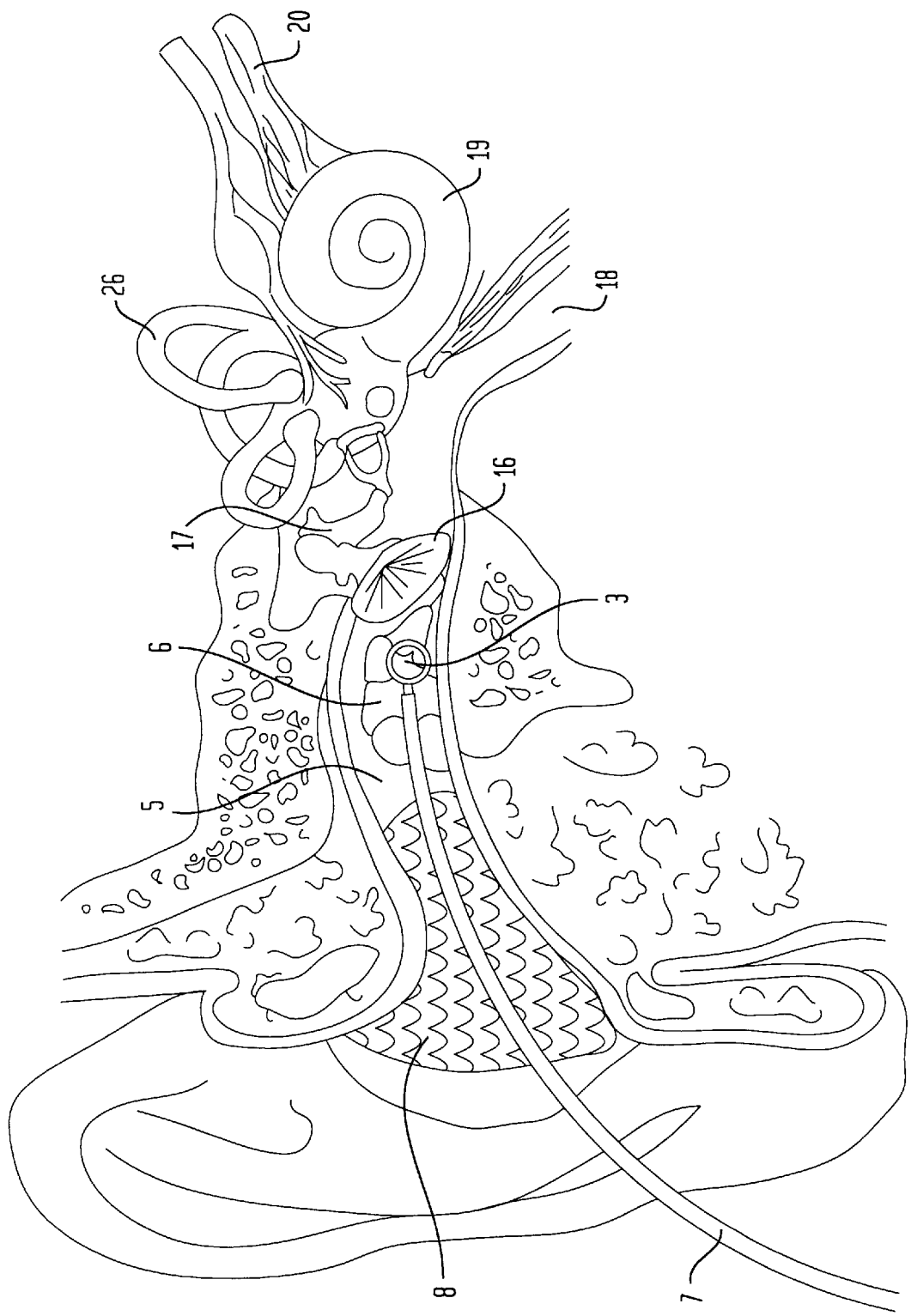
FIG. 4a is a sectional view through the external and internal auditory meatus of a human being, illustrating the placement of an electrode of the stimulating apparatus in the external auditory meatus.

As shown in FIG. 4a, the conductors 7 are directed into the auditory meatus 5 of each ear of the child and terminate in an electrode 3 in form of a body of electrically conductive material such as e.g. graphite, metal or the like. The electrode 3 is preferably of spherical configuration and embedded inside the auditory meatus 5 within an electrolyte 6 near the ear drum 16. The inclusion of the electrode 3 in the electrolyte 6 is necessary to establish an effective electrical conduction between the electrode 3 and the body mass. A preferred electrolyte 6 is for example 0.9% of saline solution. A plastic mass 8 is placed within the external auditory meatus 5 of each ear to secure the conductors 7 and the electrode 3 in place and to possibly seal the inner ear from outside.

Figure 4B:
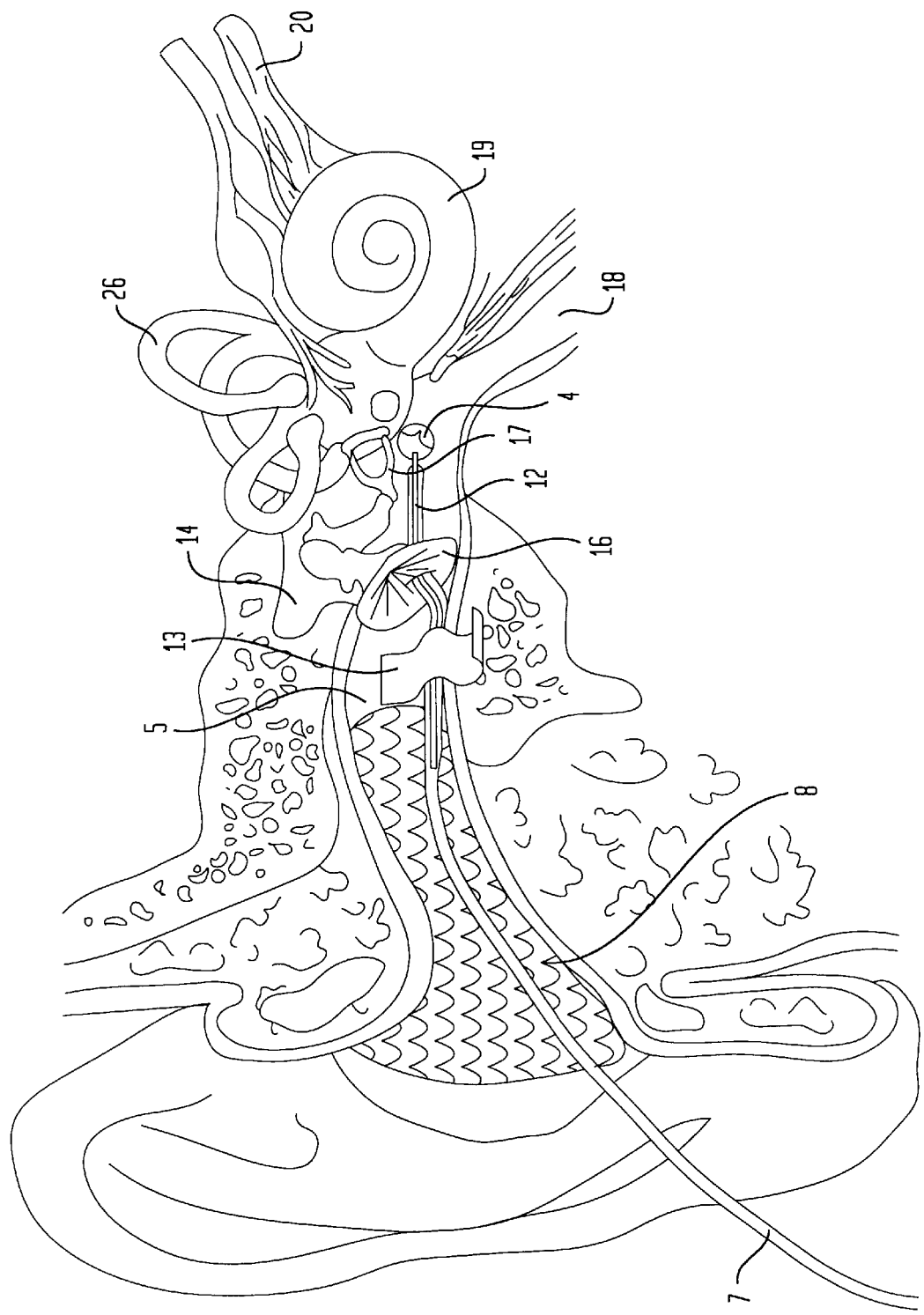
FIG. 4b is a sectional view through the external and internal auditory meatus of a human being, illustrating the placement of an electrode of the stimulating apparatus in the middle ear.

FIG. 4b shows a variation in which the stimulator-distal end of each conductor 7 is widened to include a metal rod 12 and is guided through the ear drum 16 into the middle ear comprised of the auditory ossicles 17 and the Eustachian tube 18. Further shown in FIG. 4b is the cochlea 19 as well as the nerves 20 and semicircular canals 26 which form the internal ear. The metal rod 12 projects beyond the conductor 7 and terminates in an electrode 4 which bears upon the promontory within the middle ear 14. The electrode 4 is made of a body of conductive material such as e.g. graphite, metal or the like and is of spherical configuration. The placement of the electrodes 4 inside the middle ear is particular suitable in difficult cases.

Advantageously, an adhesive strip 13 is used for properly positioning the conductor 7 and the metal rod 12 in each ear before being secured in place by the plastic mass 8 inserted in the auditory meatus 5.

The plastic body 8 is suitably made of elastic deformable material to secure the conductor 7 and possibly the metallic rod 12 in place during movements of the child. A suitable material for the plastic body 8 includes a rapidly and coldly polymerizing plastic material that resembles those materials used for sealing the auditory meatus from sound waves.

The electric circuit triggering the stimulation impulses (stimulator 1, electrical conductor 7, electrode 3, electrolyte 6, body of the patient), is closed by the mass electrode 9 which is attached upon the skin of the patient and effects a return of the stimulation currents to the stimulator 1.

Figure 5:
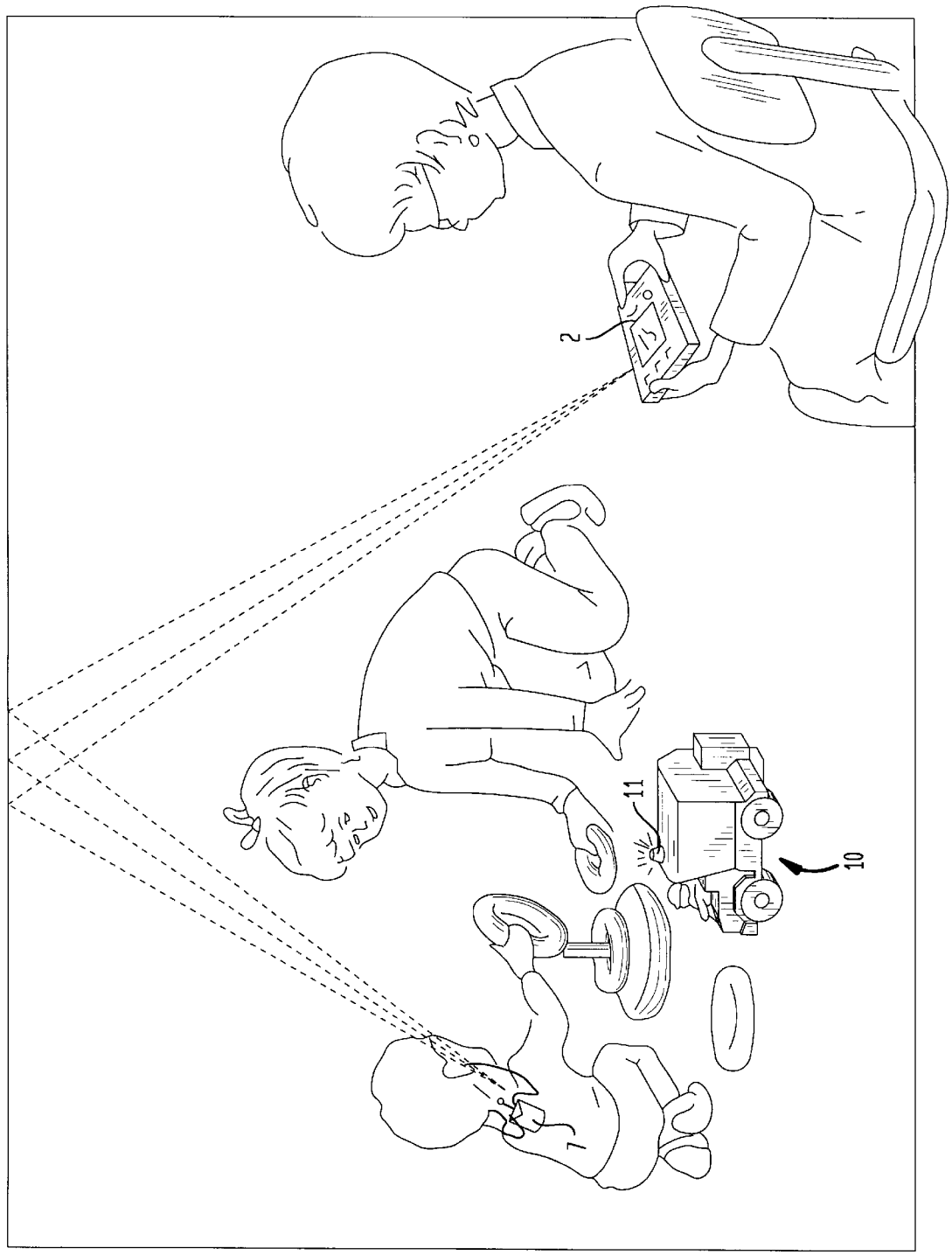
FIG. 5 is an exemplified, schematic illustration of the stimulating apparatus according to the present invention in operative mode.

The selection of parameters for the stimulation, i.e. sound frequency and sound intensity as well as time pattern of the stimulation, is inputted into the stimulator 1 by a control unit 2 through wireless transmission via electromagnetic waves in the infrared range, as indicated in FIG. 5. During examination for determination of characteristic audibility curves, the child which is equipped with the stimulator 1 can pursue any desired activity. As the stimulator 1 is very small and is free of any wired connections to the control unit 2, and as the electric conductors 7 to the various electrodes 3 or 4 and 9 are sufficiently long, the child is afforded complete freedom of movement and the normal behavior is not impeded in any way.

When, during playing, the child perceives an auditive signal, the activity is interrupted, mostly followed by a particular happy facial expression. A precise observation of the child's reactions can thus be utilized to ascertain the threshold of audibility at each frequency and to thereby determine the SL audibility curve. The UCL audibility curve can be determined in a similar manner because the facial expression and the behavior of the child changes significantly when the sound pressure reaches the threshold of an uncomfortable sound level.

When the examination for determination of the audibility curves involves particularly uncooperative young children, it has proven suitable to commence the examination in such a way that the stimulation of the auditory nerves is accompanied by an optical signal. This requires a separate optical unit which triggers a visual signal in form of an illuminating lamp 11 as soon as a stimulation impulse is transmitted. Any toy with illumination, e.g. a toy truck 10, is suitable as optical unit for infants. The triggering of a visual signal that goes hand-in-hand with the generation of a stimulation impulse is advantageous because the child realizes that an auditive perception is accompanied by a particular light so that each further auditive perception will result in the child looking for the illumination of the lamp 11. Even when shutting down the stimulation-synchronous illumination of the light, the child will continue to associate the auditive perception with the illumination of the lamp 11 of the toy truck 10 an thus automatically look for the lamp 11 so that the operator assigned to the examination for determining the audibility curves is in a position to ascertain in a particular simple manner as to whether or not a stimulation of the auditory nerve results in an auditive perception.

In order to check and verify a correct reception in the stimulator 1 of the data being transmitted from the control unit 2, the stimulator 1 is equipped with means to trigger an acoustic confirmation signal during execution of the desired stimulation. In the event the intensity of the stimulation current is reduced compared to the input in the control unit 2, e.g. due to discharged voltage source of the stimulator 1 or interruption of the stimulation current, or in the event the data transmission is upset for any reason e.g. through infrared radiation from a TV remote control or through partial screening of the receiver diode or transmitter diode, the stimulator 1 triggers a particular warning signal.

Figure 6A:
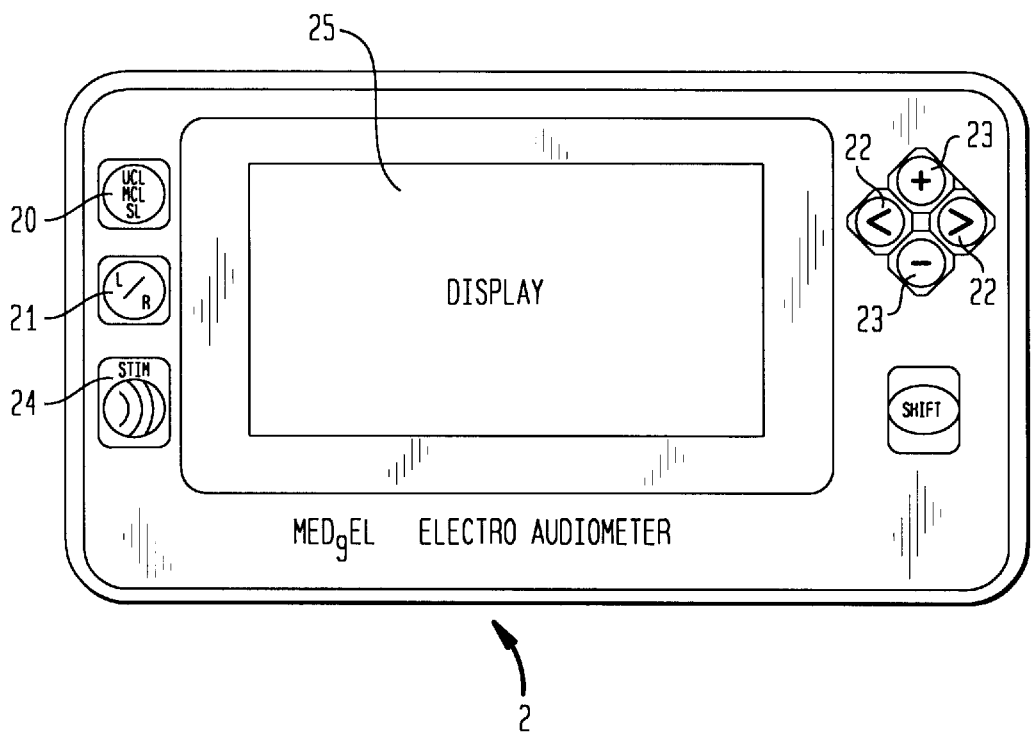
FIG. 6a is a schematic illustration of a control unit for use with the stimulating apparatus according to the present invention.

Turning now to FIG. 6a, there is shown a detailed illustration of the control unit 2, including a graphic display 25 for illustration of the determined audibility curves and selected input commands for verification by the operator. The operation of the control unit 2 is attained by few input keys in the following manner:

Before commencing the examination, the type of audibility curve (SL, UCL, MCL) to be determined is selected by suitably pressing key 20. Actuation of a key 21 situated underneath the key 20 allows a selection of which of both electrodes 3, 4 on the left or the right side of the ear should output the stimulation impulses. The desired sound frequency is set by the frequency keys 22, while the sound intensities can be modified by the keys 23.

After inputting the required commands, a key 24 (so called STIM key) is actuated for transmitting the data to stimulator 1. After conclusion of the measurements, the result is illustrated by the graphic display 25. As a printout of the test results is typically required, the control unit 2 is provided with a terminal 57 (FIG. 6b) for connection of a printer (not shown). Thus, all audibility curves as illustrated by the graphic display 25 are printed also on hard copy.

Figure 6B:
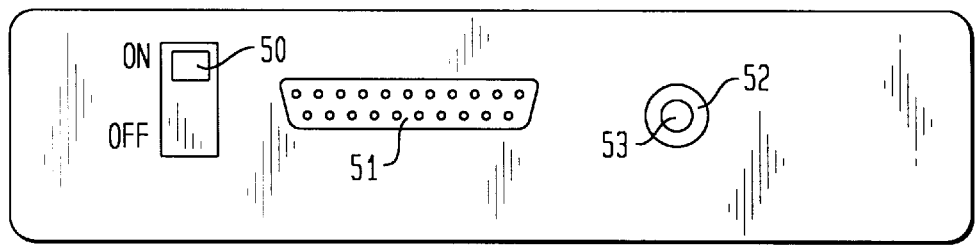

FIG. 6b shows the back panel of the control unit 2, illustrating in detail the ON-OFF switch 50, the printer terminal 57 and a bore 52 for allowing unobstructed transmission of signals emitted from the infrared transmitter diode 53 to the stimulator 1 for inputting desired commands.

Turning now to FIG. 7, there is shown an exemplified circuitry in form of a block diagram for the stimulator 1. The signal as transmitted from the control unit 2 is received by an infrared diode 30 of the stimulator and demodulated by demodulator 31 for input into decoder 32 which translates the inputted data in a digital data word and checks it for validity. Subsequently, the data word is stored in register 34. If the received data word is valid, a buzzer 38 is actuated by a respective signal via control logic 33. Preferably, the transmission of the data word is executed twice in series so that the sounding of two sounds confirms two successive correct receptions.

The absence of this signal indicates a failed transmission e.g. a screening of the receiver diode, interfering signals e.g. from a TV remote control, etc.

The stimulator 1 further includes a frequency generator 35 which generates a reference signal of constant frequency for input into a counter 36 for splitting the frequency of this signal to thereby generate signals of frequencies required for the stimulation. Bits A, B and C of the digital data word stored in register 34 control a multiplexer 37 which connects the frequency, commensurate with the value of A, B, C, with the reference voltage input of a digital/analog converter (DAC) 44. The digital input of DAC 44 is connected to the bits of the data word which determines the sound intensity so that the output of DAC 44 generates an analog signal of predetermined amplitude and frequency. This signal is amplified by a current output stage 39 and connected with the electrode 3, 4 of the desired auditory meatus (right or left) by a switch 40.

The current actually flowing through the electrode 3, 4 is sensed by a comparator 42 for comparison with a threshold value 43. If the current flowing through the electrode 3, 4 is too small and thus the sound intensity of the executed stimulation insufficient, buzzer 38 is activated by comparator 42 to trigger a respective warning signal.

While the invention has been illustrated and described as embodied in an apparatus for electric stimulation of auditory nerves of a human being, it is not intended to be limited to the details shown since various modifications and structural changes may be made without departing in any way from the spirit of the present invention.

What is claimed as new and desired to be protected by Letters Patent is set forth in the appended claims:

1. Method for testing a response of auditory nerves of a human being to an electric stimulation signal, comprising:

placing an electrode within the human ear of a hearing impaired human being, said electrode contacting areas in the human ear susceptive to stimulation by said electric stimulation signal;

applying to said electrode electric signals having a plurality of frequencies and a plurality of intensities for eliciting a sensory response from said human being as a function of said frequencies and intensities for deriving characteristic features of audibility curves for said human being;

comparing said sensory response from said human being to audibility curves derived at approximately identical frequencies of healthy human beings; and predicting from said comparison the likelihood of success of a permanent cochlear implant for said hearing impaired human being.

2. The method of claim 1, wherein said frequencies are in a range between about 60 Hz and 2 kHz.

3. The method of claim 1, wherein said electrode is placed in the auditory meatus of the human ear.

4. The method of claim 1, wherein said audibility curves comprise SL-, MCL- and UCL-audibility curves of the auditory meatus of said human being.

5. The method of claim 1, wherein placing the electrode further comprises embedding the electrode in an electrolyte body and sealing the auditory meatus from the outside with a plastic body.

6. The method of claim 1, wherein said electrical signals are transmitted to said electrode by a detachable stimulator.

7. The method of claim 1, wherein eliciting a response further comprises optically signaling during transmission of said stimulation signals.

8. The method of claim 7, wherein said optical signaling is provided by a toy suitable for infants.

9. The method of claim 8, wherein said optical signaling is provided by a toy truck.

* * * * *